US009319593B2

(12) United States Patent
Shinji et al.

(10) Patent No.: US 9,319,593 B2
(45) Date of Patent: Apr. 19, 2016

(54) RECOGNITION APPARATUS, RECOGNITION METHOD, MOUNTING APPARATUS, AND MOUNTING METHOD

(71) Applicant: Samsung Electronics Co., Ltd., Suwon-Si, Gyeonggi-Do (KR)

(72) Inventors: Ueyama Shinji, Yokohama (JP); Kajinami Masato, Yokohama (JP); Yukimori Yoshiaki, Yokohama (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 214 days.

(21) Appl. No.: 14/101,519

(22) Filed: Dec. 10, 2013

(65) Prior Publication Data

US 2014/0160272 A1    Jun. 12, 2014

(30) Foreign Application Priority Data

Dec. 10, 2012  (JP) ................................. 2012-269695
Nov. 29, 2013  (KR) ........................ 10-2013-0147819

(51) Int. Cl.
| H04N 7/18 | (2006.01) |
| H04N 5/232 | (2006.01) |
| G01N 21/956 | (2006.01) |
| G11B 27/00 | (2006.01) |
| H04N 5/93 | (2006.01) |

(52) U.S. Cl.
CPC ..... *H04N 5/23296* (2013.01); *G01N 21/95607* (2013.01); *G01N 2021/95661* (2013.01)

(58) Field of Classification Search
CPC ............. H04N 7/18; H04N 5/93; G11B 27/00
USPC ................... 348/61, 80, 86, 87; 386/280, 278
See application file for complete search history.

(56) References Cited

U.S. PATENT DOCUMENTS

| 6,182,069 | B1 * | 1/2001 | Niblack et al. | |
| 9,075,492 | B1 * | 7/2015 | Scott et al. | |
| 2004/0196357 | A1 * | 10/2004 | Tasaka | 347/248 |
| 2005/0285880 | A1 * | 12/2005 | Lai et al. | 345/660 |
| 2009/0052765 | A1 * | 2/2009 | Toyoda et al. | 382/149 |
| 2011/0234640 | A1 * | 9/2011 | Ishida | 345/671 |
| 2013/0003083 | A1 * | 1/2013 | Satomi | 358/1.2 |
| 2013/0155295 | A1 * | 6/2013 | Bekiares et al. | 348/240.99 |

FOREIGN PATENT DOCUMENTS

| JP | 07-320062 | 12/1995 |
| JP | 2005-093839 A | 4/2005 |
| JP | 2011-075310 A | 4/2011 |

* cited by examiner

*Primary Examiner* — Daquan Zhao
(74) *Attorney, Agent, or Firm* — Harness, Dickey & Pierce, P.L.C.

(57) ABSTRACT

The recognition and mounting apparatus including a zoom lens capable of changing imaging magnification, a chip camera, having a plurality of imaging pixels, capable of capturing an image an IC chip having a plurality of bumps arranged at at least one interval, through the zoom lens, a storage unit for storing shape information of the IC chip including at least information indicating an arrangement interval between the plurality of bumps, and a signal processor adjusting imaging magnification of the zoom lens based on a length of the imaging pixel and the information indicating the arrangement interval stored in the storage unit, and recognizing a position of the bump based on a plurality of pixel values in the image captured by the chip camera may be provided.

13 Claims, 7 Drawing Sheets

RECOGNITION APPARATUS, RECOGNITION METHOD, MOUNTING APPARATUS, AND MOUNTING METHOD

CROSS-REFERENCE TO RELATED APPLICATIONS

This application claims under 35 U.S.C. §119 to Japanese Patent Application No. 2012-0269695, filed on Dec. 10, 2012, in the Japanese Patent Office, and Korean Patent Application No. 10-2013-0147819, filed on Nov. 29, 2013, in the Korean Intellectual Property Office, the disclosures of which are incorporated herein in their entireties by reference.

BACKGROUND

The inventive concepts relate to recognition apparatuses, recognition methods, mounting apparatuses, and/or mounting methods.

Japanese Patent Publication No. hei 7-320062 describes, when a semiconductor chip is mounted to a circuit board, a grasp posture of the semiconductor chip while being carried toward the circuit board is recognized. In a recognition apparatus disclosed in Japanese Patent Publication No. hei 7-320062, a bottom surface of a ball grid array type package is imaged, and a gradient of the image of solder balls is measured, thereby recognizing the posture of the package. At this time, the position of the semiconductor chip is estimated from a plurality of center of gravity positions of the solder balls in the image, by linear fitting using a least-square method.

Japanese Patent Publication No. 2005-93839 describes that recognition accuracy is improved by enhancing contrast in a captured image, in position recognition of a plurality of solder bumps included in a semiconductor chip.

Japanese Patent Publication No. 2011-75310 describes a configuration in which lens magnification with respect to a test object having a cyclic pattern is finely adjusted.

In recognition apparatuses described in, for instance, Japanese Patent Publication No. hei 7-320062 and Japanese Patent Publication No. 2005-93839, a semiconductor chip is imaged using an imaging sensor having a plurality of imaging pixels. A recognition process is performed on a plurality of formations on the semiconductor chip, for instance, a solder bump included in the captured image. A connection portion formed in the semiconductor chip, for instance, the solder bump, becomes smaller. Accordingly, if the numbers of pixels of the imaging sensors are identical, as the connection portion decreases in size, the number of pixels allocated for each solder bump or for each pitch between the solder bumps also decreases. Accordingly, the following problems may arise due to, for instance, a decrease of the size of the connection portion.

The accuracy of position recognition in a case where the arrangement of the solder bumps conforms to image sampling may be lower than that in a case where the arrangement of the solder bumps does not conform to the image sampling. Here, the case where the arrangement of the solder bumps conforms to the image sampling means that the number of imaging pixels corresponding to each pitch of the arrangement of the solder bumps is constantly maintained. Assuming that a position at which the number of pixels are set to a peak corresponds to the position of the center (the position of a peak) of the solder bump and that two pixels have a peak value (or a value close thereto) on average in the vicinity of the center of the solder bump, when the arrangement of the solder bumps conforms with the image sampling, there is the possibility that two pixels constantly (or, constantly and repeatedly) have values close to the peak value with respect to the plurality of solder bumps. When the arrangement of the solder bumps and the image sampling do not conform to each other, however, there is a high possibility that variations may occur for each solder bump such that, for example, one to three pixels have a peak value. Accordingly, an error in position recognition is less than two pixels when the arrangement of the solder bumps and the image sampling conform to each other, and is less than one to three pixels when the arrangement of the solder bumps and the image sampling do not conform to each other. For example, when a plurality of solder bumps having an error of less than one pixel are present, a deviation of the position or direction of each solder bump may be estimated with a high level of accuracy. Therefore, the accuracy of position recognition in a case where the arrangement of the solder bumps conforms to the image sampling may be lower than the accuracy of position recognition in a case where the arrangement of the solder bumps does not conform to the image sampling.

SUMMARY

The inventive concepts provides recognition apparatuses, recognition methods, mounting apparatuses, and/or mounting methods, which are capable of reducing or preventing a decrease in the accuracy of position recognition that may occur when a correspondence relation between an arrangement of an object to be recognized and a plurality of imaging pixels satisfies a specific condition.

According to example embodiments of the inventive concepts, a recognition and mounting apparatus may include an imaging magnification adjustment unit configured to change an imaging magnification, an imaging unit having a plurality of imaging pixels and configured to image an object to be recognized through the imaging magnification adjustment unit, the object having a plurality of recognizable features to be recognized, the recognizable features provided at at least one arrangement interval, a storage unit configured to store a shape information of the object to be recognized, the shape information including at least information indicating the arrangement interval between the recognizable features, and a signal processor configure to adjust the imaging magnification of the imaging magnification adjustment unit based on a length of the imaging pixel and the shape information stored in the storage unit, and configured to recognize positions of the first recognizable features based on a plurality of pixel values in the image captured by the imaging unit.

According to example embodiments, the signal processor may be configured to adjust imaging magnification of the imaging magnification adjustment unit such that the arrangement interval and an integer multiple of the length of the imaging pixel do not conform to each other in the image captured by the imaging unit.

According to example embodiments of the inventive concepts, the recognition and mounting apparatus may further include a mounting apparatus configured to mount an object to be recognized to a circuit board by performing a correction control according to a position or an angle of the object to be recognized, based on results of the recognizing by the signal processor. The object to be recognized may include a semiconductor chip.

According to example embodiments of the inventive concepts, a recognition and mounting method may include changing an imaging magnification using an imaging magnification adjustment, capturing an image, using an imaging unit having a plurality of imaging pixels, an object to be recognized having a plurality of recognizable features through the imaging magnification adjustment unit, the recognizable features being provided at at least one arrangement interval, storing, using a storage unit, a shape information of the object, the shape information including at least information indicating the arrangement interval between the recognizable features; adjusting, using a signal processor, the imaging magnification of the imaging magnification adjustment unit based on a length of the imaging pixel and information indicating the shape information stored in the storage unit, and recognizing, using a signal processor, positions of the recognizable features based on a plurality of pixel values in the image captured by the imaging unit.

The recognition and mounting method may further include adjusting, using a signal processor, the imaging magnification of the imaging magnification adjustment unit such that that the arrangement interval and an integer multiple of the length of the imaging pixel do not conform to each other in the image captured by the imaging unit.

According to example embodiments of the inventive concepts, the recognition and mounting method may include mounting the object to be recognized onto a circuit board by performing correction control according to a position or an angle of the object to be recognized, based on results of the recognizing. The object to be recognized may include a semiconductor chip.

BRIEF DESCRIPTION OF THE DRAWINGS

Example embodiments of the inventive concept will be more clearly understood from the following detailed description taken in conjunction with the accompanying drawings in which.

DETAILED DESCRIPTION OF THE EMBODIMENTS

Various example embodiments will be described more fully hereinafter with reference to the accompanying drawings, in which some example embodiments are shown. Example embodiments may, however, be embodied in many different forms and should not be construed as limited to the example embodiments set forth herein. Rather, these example embodiments are merely provided so that this disclosure will be thorough and complete, and will fully convey the scope of example embodiments to those skilled in the art. In the drawings, the sizes and relative sizes of the various layers and regions may have been exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
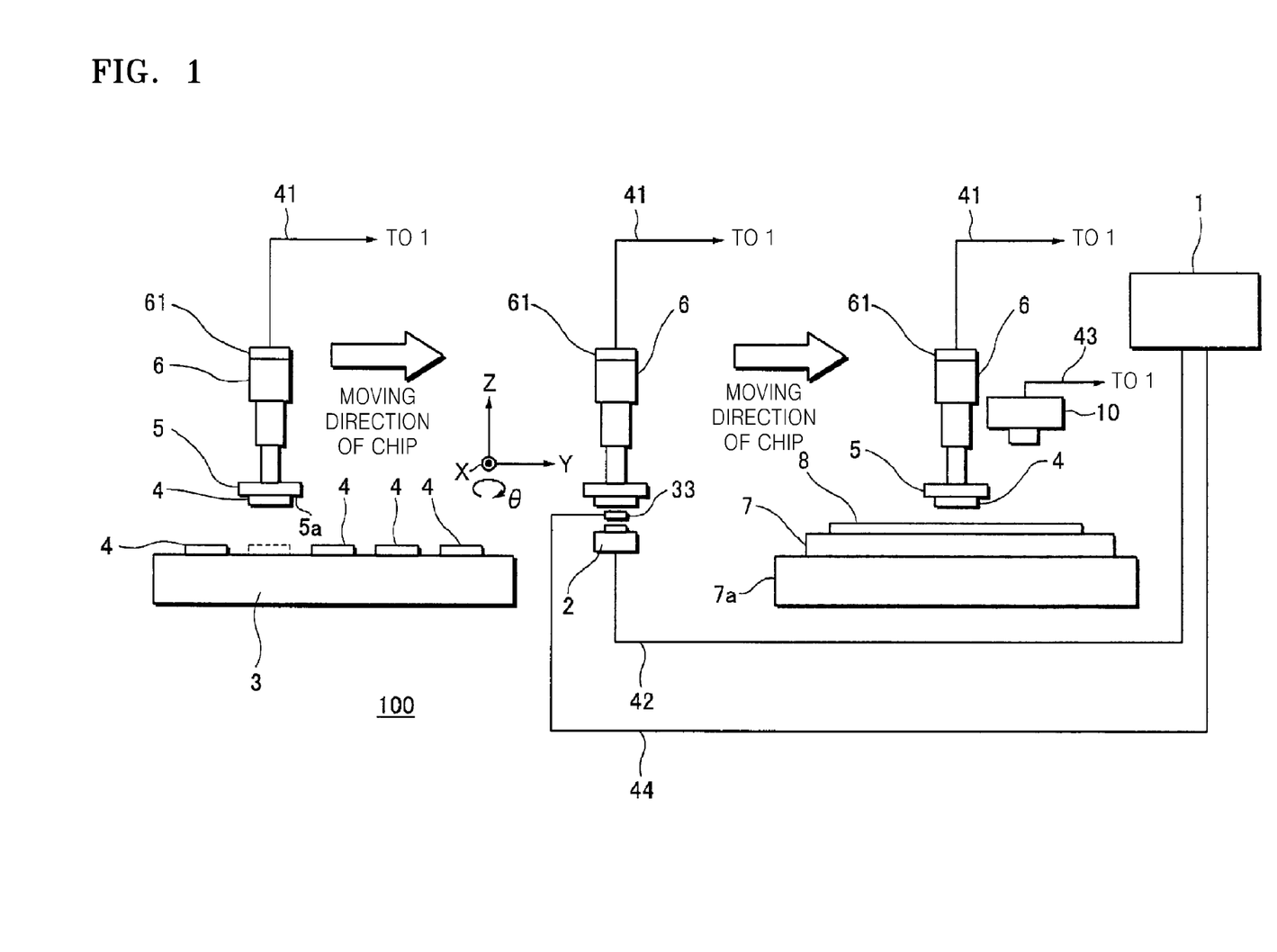
FIG. 1 is a schematic diagram illustrating a configuration of a mounting apparatus according to example embodiments.

Hereinafter, example embodiments of the inventive concepts will be described with reference to the accompanying drawings. FIG. 1 is a schematic diagram illustrating a configuration of a mounting apparatus 100 (recognition apparatus) according to example embodiments. The mounting apparatus 100 illustrated in FIG. 1 is an apparatus for mounting an integrated circuit (IC) chip 4 (semiconductor chip) to a circuit board 8. The mounting apparatus 100 includes a signal processor 1, a chip camera 2, a zoom lens 33, a movement unit 6, a motion controller 61, a substrate stage 7, a fixing board 7a, a place camera 10, and the like.

The signal processor 1 performs a desired (or, alternatively predetermined) recognition process on image signals acquired from the chip camera 2 and the place camera 10, and controls the motion controller 61 and the like based on results of the recognition or design information of the IC chip 4 or the circuit board 8. The signal processor 1 is connected to the motion controller 61 through a cable 41. In addition, the signal processor 1 is connected to the chip camera 2 through a cable 42. The signal processor 1 is connected to the zoom lens 33 through a cable 44.

The motion controller 61 is configured to include a driving mechanism using, e.g., a motor, moves the movement unit 6 in response to an instruction of the signal processor 1 in a direction of an arrow or in each of X, Y, and Z directions shown by a circle, and changes a direction 8 on an XY plane. In other words, the movement unit 6 may move by a desired (or, alternatively predetermined) distance in a depth front-back direction (X direction), a horizontal direction (Y direction), and a vertical direction (Z direction) toward the drawing, and may change a direction 8 of an adsorption head 5 in a desired (or, alternatively predetermined) angle range. Meanwhile, a positive direction of an X-axis is a direction toward the front side from the back side, and positive directions of a Y-axis and a Z-axis are a direction of an arrow.

The movement unit 6 is configured to include the adsorption head 5 at a tip portion thereof. The adsorption head 5 adsorbs the IC chip 4. FIG. 1 illustrates a state where one movement unit 6 adsorbs and lifts up the IC chip 4 from a chip cassette 3 (left movement unit 6), a state where the movement unit 6 passes over the chip camera 2 (central movement unit 6), and a state where the movement unit 6 moves over the circuit board 8 (right movement unit 6). The chip cassette 3, the chip camera 2, the circuit board 8, the place camera 10, and the like are arranged to have the positional relation illustrated in FIG. 1.

The adsorption head 5 is configured to include an adsorption surface 5a formed of, for example, a porous metal. The adsorption head 5 attaches the IC chip 4 to the adsorption surface 5a using negative pressure. In addition, the adsorption head 5 is heated in a state where the IC chip 4 is placed on the circuit board 8, and thus a plurality of solder bumps included in the IC chip 4 are thermo-compression bonded to a desired (or, alternatively predetermined) contact point on the circuit board 8. Meanwhile, a mark serving as a reference when recognizing an attachment state of the IC chip 4 is shown in the adsorption surface 5a.

The chip cassette 3 is a container accommodating the plurality of IC chips 4. A top surface (that is, in an upward Z-axis direction) of the chip cassette 3 is opened.

The IC chip 4 is a semiconductor IC chip. In the current embodiment, the IC chip 4 has a structure referred to as a wafer level chip size (or scale) package (WLCSP). The plurality of solder bumps are formed in a rear surface (a downward surface of the drawing, that is, a surface opposite to a surface to which the adsorption head 5 is attached) of the IC chip 4. The IC chip 4 is adsorbed to the adsorption head 5 and is lifted upward in the Z-direction, from a state where the IC chip 4 is accommodated in the chip cassette 3. In this state, the IC chip 4 passes over the top of the chip camera 2 and is then transferred to the top of the circuit board 8.

The circuit board 8 is placed on the substrate stage 7. The substrate stage 7 is supported by the fixing board 7a so as to be finely adjusted in the X and Y directions.

The place camera 10 is a camera that images the circuit board 8. The signal processor 1 performs a position recognition process on the vicinity of a connection portion with the IC chip 4, based on an image signal acquired from the place camera 10, to calculate an amount of positional deviation or angular deviation from a desired (or, alternatively predetermined) reference of the circuit board 8.

Figure 2:
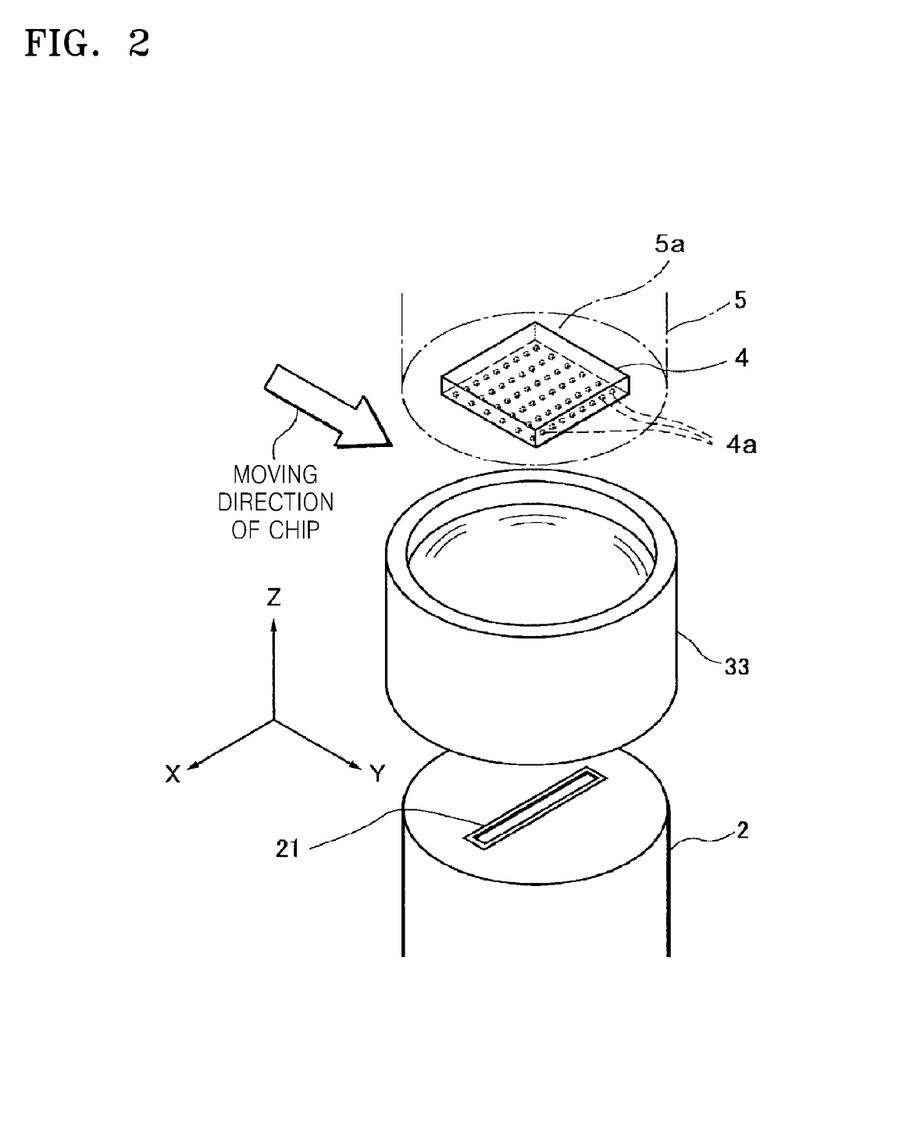
FIG. 2 is a schematic perspective view illustrating a positional relation between a chip camera, a zoom lens, and an integrated circuit (IC) chip, which are illustrated in FIG. 1.

The chip camera 2 captures an image of the IC chip 4 which is attached to the adsorption head 5 and is being moved, and outputs an image signal of the captured image to the signal processor 1. The chip camera 2 is provided at a desired (or, alternatively predetermined) position between an installation position of the chip cassette 3 and an installation position of the circuit board 8. The chip camera 2 images a rear surface of the IC chip 4, through a zoom lens 33. The zoom lens 33 includes a plurality of lenses and a lens moving mechanism. The zoom lens 33 is a lens group that may arbitrarily change a focal length of a lens group in a fixed range and does not move a focal surface (that is, does not displace a focus). The zoom lens 33 may change the focal length in response to a desired (or, alternatively predetermined) control signal which is input from the outside. The signal processor 1 transmits the desired (or, alternatively predetermined) control signal through the cable 44 to change the focal length (that is, imaging magnification of the chip camera 2) of the zoom lens 33. FIG. 2 is a schematic perspective view illustrating a positional relation between the chip camera 2, the zoom lens 33, and the IC chip 4, which are illustrated in FIG. 1. In addition, in FIGS. 1 and 2, the same components are denoted by the same reference numerals. Furthermore, directions of X, Y, and Z arrows correspond to the directions of X, Y, and Z axes illustrated in FIG. 1, respectively. In addition, although the chip camera 2 and the zoom lens 33 are formed to be separated from each other in FIGS. 1 and 2, the chip camera 2 and the zoom lens 33 may be formed integrally.

The chip camera 2 may be configured to include a line sensor 21. The line sensor 21 may be configured such that a plurality of imaging pixels formed of a solid-state imaging device, e.g., a complementary metal oxide semiconductor (CMOS) or a charge coupled device (CCD), are arranged in a single column or a plurality of columns in order to ensure an exposure time. The chip camera 2 may repeatedly output, with a desired (or, alternatively predetermined) period, each pixel value which indicates a size of an electrical signal obtained by performing photoelectric conversion on incident light on each of pixels constituting the line sensor 21. For example, the line sensor 21 may output a monochrome image signal having a multi-value gradation (e.g., grayscale). Therefore, a pixel value of each of pixels output by the line sensor 21 may indicate a luminance value. According to example embodiments, the IC chip 4 may be adsorbed onto the adsorption surface 5a of the adsorption head 5 such that the rear surface thereof (e.g., the surface having a plurality of bumps 4a arranged thereon) faces downward (e.g., faces toward the chip camera 2). The chip camera 2 may repeatedly output the pixels of the line sensor 21 multiple times with a desired (or, alternatively predetermined) period such that the IC chip 4 is moving at a desired (or, alternatively predetermined) speed in an IC chip moving direction (e.g., Y-axis direction) as indicated by an arrow in FIG. 2.

Figure 3:
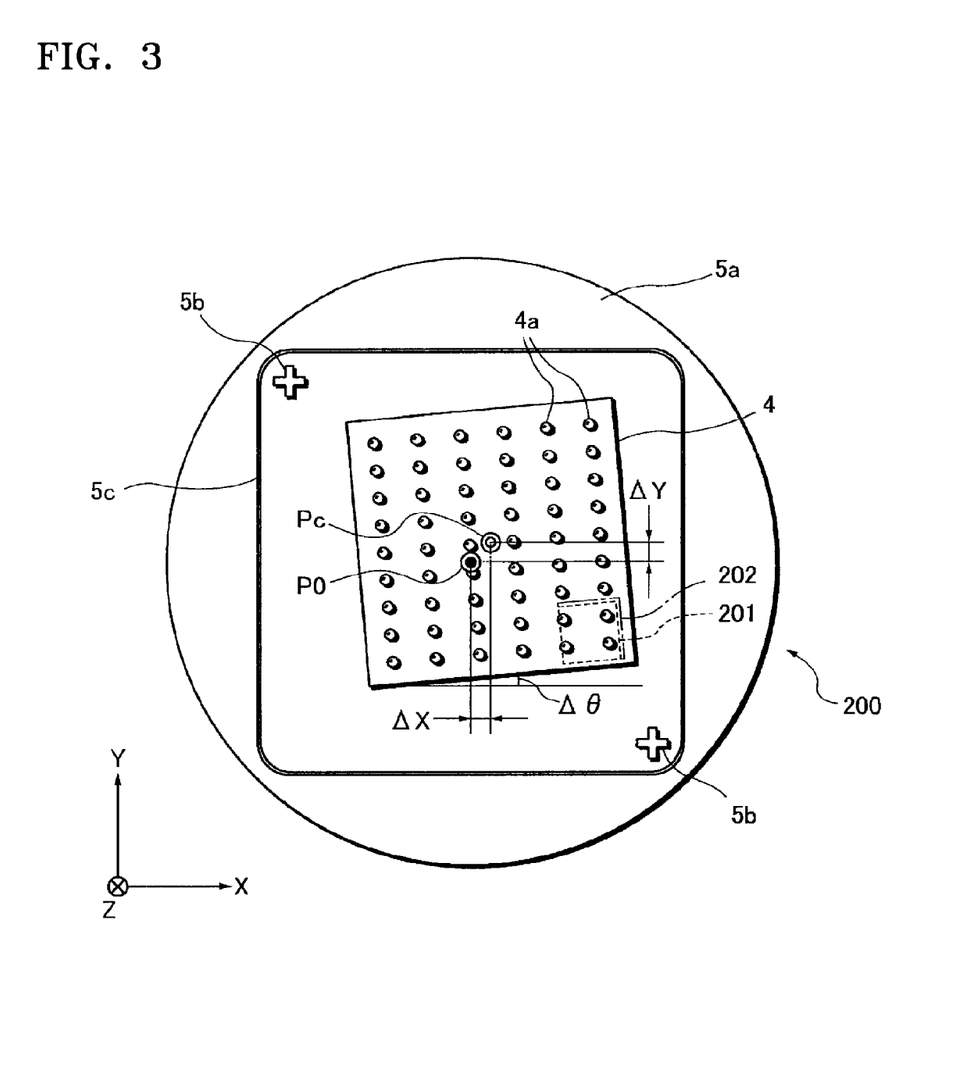
FIG. 3 is a schematic diagram illustrating an example of a captured image obtained by the chip camera illustrated in FIG. 1.

FIG. 3 is a schematic diagram illustrating an example of a captured image 200 obtained by the chip camera 2 illustrated in FIG. 1. In FIG. 3, the X, Y, and Z directions illustrated in FIG. 1 correspond to directions indicated by arrows for the X and Y directions and a circle for the Z direction. Meanwhile, in FIG. 3, a positive direction of each of the X and Y axes is a direction of an arrow, and a positive direction of the Z axis is a direction from the back side toward the front side. In the example illustrated in FIG. 3, the captured image 200 may include an image of the entire rear surface of the IC chip 4 and/or may include an image of substantially the entire portion of the adsorption surface 5a. A pair of signs 5b and a reference line 5c indicating a reference region may be marks that are actually provided on the adsorption surface 5a. These marks may serve as references when recognizing an attachment state of the IC chip 4. However, both the signs 5b and the reference line 5c may not be provided. Further, as illustrated in FIG. 3, the IC chip 4 may include the plurality of bumps 4a that are arranged, for instance, at regular intervals in the X and Y directions.

Figures 4A, 4B:
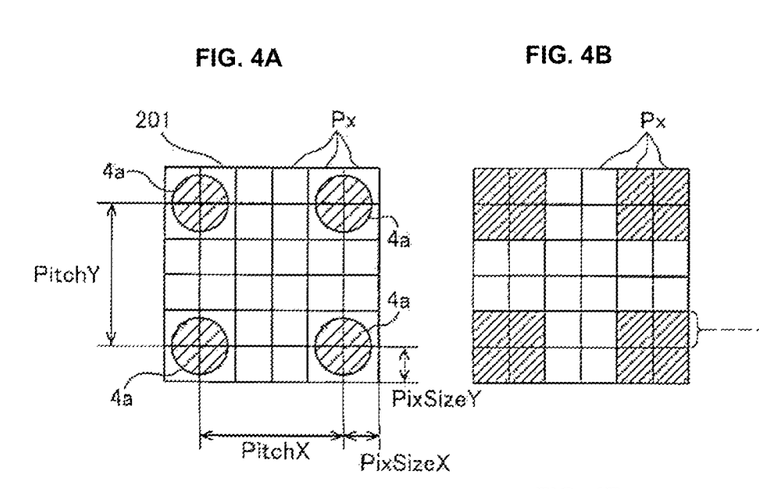
FIGS. 4A to 4F are schematic diagrams illustrating images obtained by capturing images of partial regions of the rear surface of the IC chip 4 illustrated in FIG. 3, using the line camera and zoom lens illustrated in FIGS. 1 and 2.
Figure 4C:
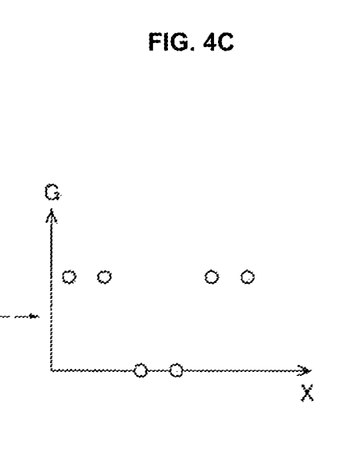
Figures 4D, 4E:
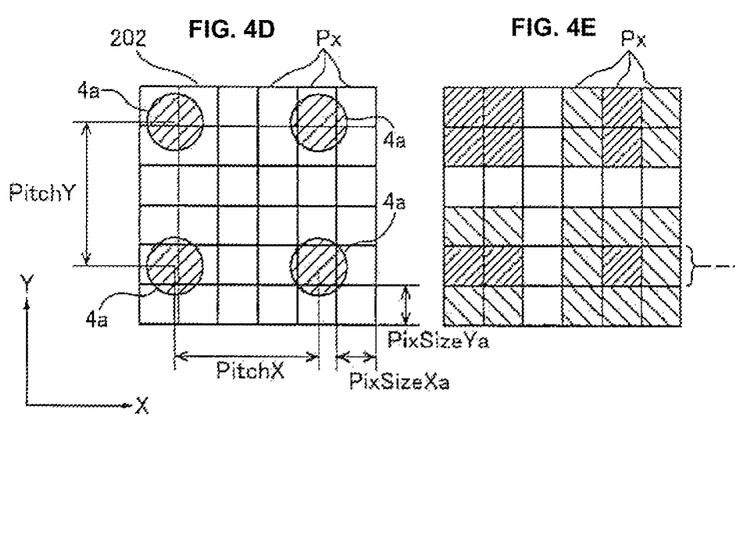
Figure 4F:
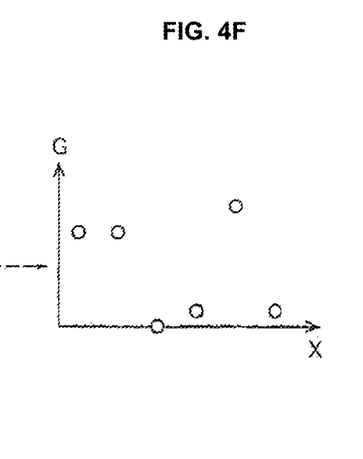

Next, operation of the zoom lens 33 will be described with reference to FIGS. 4A to 4F. FIGS. 4A to 4F are schematic diagrams illustrating images obtained by capturing images of partial regions 201 and 202 of the rear surface of the IC chip 4 illustrated in FIG. 3, using a line camera 2 and zoom lens 33 illustrated in FIGS. 1 and 2. FIGS. 4A to 4C are schematic diagrams of an image captured at any imaging magnification A, and FIGS. 4D to 4F are schematic diagrams of an image captured at another imaging magnification B (and satisfies the relation of B<A). FIG. 4A is a schematic diagram illustrating a correspondence relation between four bumps 4a within the region 201 and pixels Px when the region 201 shown by a dotted line in FIG. 3 is imaged by a total of thirty-six pixels of 6×6 pixels in the X and Y directions. FIG. 4B is a schematic diagram illustrating pixel values of the pixels Px illustrated in FIG. 4A. FIG. 4B shows that the pixel values of the four hatched pixels Px at four corners are greater than the pixel values of other pixels Px (white pixels). FIG. 4C is a schematic diagram illustrating pixel values G of six pixels Px of the second line from the bottom of FIG. 4B.

FIG. 4D is a schematic diagram illustrating a correspondence relation between four bumps 4a and the pixels Px when the region 202 shown by a dot-dashed line within the region 202 in FIG. 3 is imaged by a total of thirty-six pixels of 6×6 pixels in the X and Y directions. In addition, in FIG. 4D, each pixel having a large size is shown in association with a difference in area between the region 201 and the region 202 (here, the area of the region 201<the area of the region 202) (in other words, an area of an imaging region for each pixel in FIG. 4D is wider than that in FIG. 4A). FIG. 4E is a schematic diagram illustrating pixel values of the pixels Px illustrated in FIG. 4D. FIG. 4E shows that pixel values of a total of nine hatched pixels Px shown by a rising diagonal stroke from bottom left to top right may be greater than pixel values of other pixels Px. Pixel values of eleven white pixels Px may be minimum values, and pixel values of sixteen hatched pixels Px shown by a falling diagonal stroke from top left to bottom right may have pixel values therebetween. FIG. 4F is a schematic diagram illustrating pixel values G of six pixels Px of the second line from the bottom of FIG. 4E.

FIGS. 4A to 4C show a case where the arrangement of the solder bumps 4a conforms to image sampling. That is, with regard to the X direction, a pitch PitchX between the solder bumps 4a corresponds to four sizes PixSizeX of imaging pixels Px. Similarly, with regard to the Y direction, a pitch PitchY between the solder bumps 4a corresponds to four sizes PixSizeY of the imaging pixels Px. In this case, pixel values of the pixels Px repeatedly have the same values with respect to other solder bumps 4a, for example, as illustrated in FIG. 4C. That is, in this case, pixel values G of two pixels corresponding the right solder bump 4a and pixel values G of two pixels corresponding to the left solder bump 4a have the same values.

FIGS. 4D to 4F show a case in which the arrangement of the solder bumps 4a does not conform to an image sampling. For example, with regard to the X direction, the pitch PitchX between the solder bumps 4a may not conform to a length corresponding to an integer multiple of a size PixSizeXa of the imaging pixel Px. Similarly, with regard to the Y direction, the pitch PitchY between the solder bumps 4a may not conform to a length corresponding to an integer multiple of a size PixSizeYa of the imaging pixel Px. In this case, pixel values of the pixels Px may vary with respect to different solder bumps 4a, for example, as illustrated in FIG. 4F. In this case, a maximum value of the pixel values G corresponding to the right solder bump 4a may be greater than a maximum value of the pixel values G corresponding to the left solder bump 4a. Comparing FIG. 4F and FIG. 4C, a variation of the pixel values corresponding to solder bumps 4a is greater in FIG. 4f. Thus, the greater variation of the pixel values in FIG. 4F may affect the accuracy of position recognition of the recognition apparatus compared to in FIG. 4C.

Consequently, according to example embodiments, the signal processor 1 adjusts the focal length of the zoom lens 33 (e.g., the imaging magnification of the chip camera 2) so that the arrangement of the solder bumps 4a does not conform to the image sampling based on length of the imaging pixel Px (PixSizeX or PixSizeXa, or PixSizeY or PixSizeYa), The length of the imaging pixel Px depends on the imaging pixel Px and desired (or, alternatively predetermined) information, which indicates an interval (PitchX or PitchY) between the solder bumps 4a and stored in a storage unit within the signal processor 1.

Figure 5:
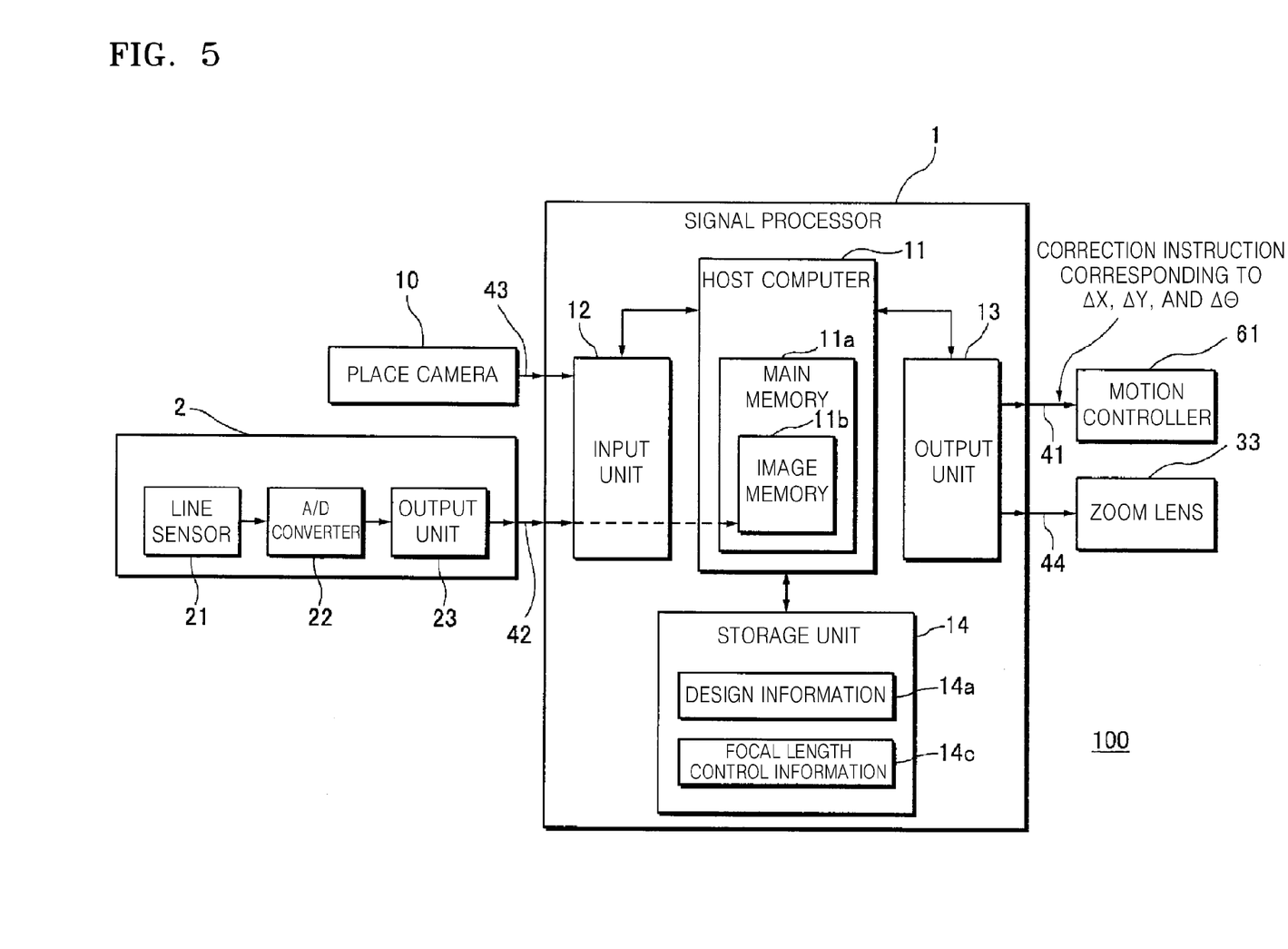
FIG. 5 is a block diagram illustrating an internal configuration example of the mounting apparatus illustrated in FIGS. 1 and 2, according to example embodiments.

FIG. 5 is a block diagram illustrating operation of the zoom lens illustrate in FIGS. 1 and 2, according to example embodiments. FIG. 5 illustrates an internal configuration of the mounting apparatus 100 depicted in FIG. 1. The signal processor 1 may include a host computer 11, an input unit 12, an output unit 13, and a storage unit 14. The host computer 11 may include a main memory 11a, and the main memory 11a may include an image memory 11b. The host computer 11 may include a central processing unit (CPU) (not shown) and executes a desired (or, alternatively predetermined) program stored in the storage unit 14 to control each unit. The input unit 12 may be an interface for inputting a signal from the place camera 10 and the chip camera 2 to the host computer 11. Pieces of image data indicating images captured by the place camera 10 and the chip camera 2 may be input to the input unit 12.

The output unit 13 may be an interface for outputting a signal from the host computer 11 to the motion controller 61 and the zoom lens 33. The output unit 13 may output information (e.g., the amount of correction corresponding to ΔX, ΔY and Δθ, or a signal for instructing the amount of correction), which indicates the amount of correction for correction control of a positional deviation and an angular deviation of the movement unit 6, to the motion controller 61. For example, the output unit 13 may output a signal for changing the focal length of the zoom lens 33.

Information (ΔX, ΔY and Δθ) indicating the amount of correction for correcting a positional deviation and an angular deviation will be described with reference to FIG. 3. In FIG. 3, a reference point P0 is a point corresponding to a rotation center of the adsorption head 5 in a θ direction. A coordinate value of the reference point P0 may be calculated with respect to the reference sign 5b or the reference line 5c on the adsorption surface 5a. A center point Pc is a point corresponding to a center point (or a center of gravity point) of the IC chip 4. A coordinate of the center point Pc may be calculated with respect to coordinate values of the plurality of solder bumps 4a recognized from an image captured by the chip camera 2 and a design value (or a measured value of another IC chip 4 serving as a reference). Here, ΔX denotes the amount of deviation of the center point Pc with respect to the reference point in an X direction, ΔY denotes the amounts of deviation of the center point Pc with respect to the reference point P0 and in a Y direction, and ΔX and ΔY are calculated as a deviation of a coordinate value of the center point Pc with respect to the reference point P0 and. Δθ is calculated as a difference between a reference direction of the IC chip 4 and an actual direction. Δθ may be calculated based on coordinate values of the plurality of solder bumps 4a recognized from the image captured by the chip camera 2 and a design value of a relationship between the coordinates and the arrangement of the solder bumps 4a (or a measured value of another IC chip 4 serving as a reference).

In FIG. 5, the storage unit 14 may be, for example, a non-volatile memory, and may store design information 14a and focal length control information 14c. The design information 14a may include information as to, e.g., the chip cassette 3, the IC chip 4, or the circuit board 8. The focal length control information 14c may include information used when instructing an adjustment of the focal length of the zoom lens 33, as described above with reference to FIG. 4. For example, the focal length control information 14c may be configured as a table that stores a correspondence relation between an identification number of the IC chip 4, information indicating a specification of the chip camera 2, and a focal length to be set.

Although not shown in FIG. 1, the signal processor 1 may include, for example, an interface for transmitting a desired (or, alternatively predetermined) control signal to the place camera 10 or the chip camera 2, and an interface for receiving a desired (or, alternatively predetermined) control signal from the motion controller 61, in addition to the above-described components. For example, the storage unit 14 may store information for controlling the motion controller 61. The design information 14a may include information with regard to external forms of the chip cassette 3, the IC chip 4 and the circuit board 8, a reference mark, a shape or position of each connecting terminal, and a setting value at the time of thermo-compression bonding. The design information may not be limited to a design value in the drawing, and may include measured values of a real IC chip 4 serving as a reference.

The chip camera 2 may include the line sensor 21, an analog-to-digital converter (A/D converter) 22, and/or an output unit 23. The A/D converter 22 may convert an analog pixel value of each pixel, which is output from the line sensor 21, into a digital signal. The output unit 23 may convert a digital signal output from the A/D converter 22 into a digital image signal having a desired (or, alternatively predetermined) format, and output the digital image signal. The digital image signal output by the output unit 23 may be directly stored in the image memory 11b via the input unit 12, for example, by a direct memory access (DMA) method.

Figure 6:
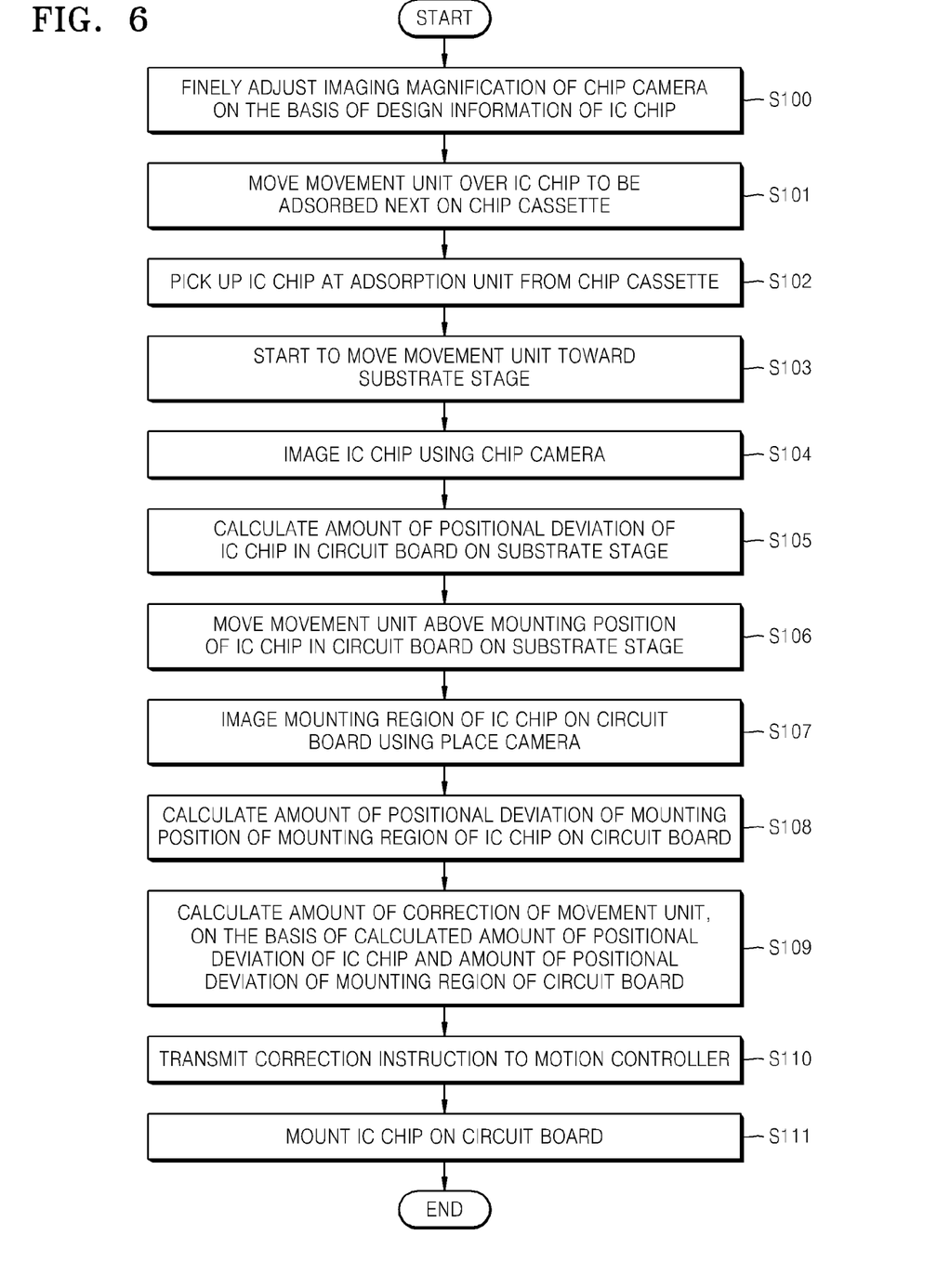
FIG. 6 is a flowchart illustrating operation of the mounting apparatus illustrated in FIGS. 1 and 5, according to example embodiments.

FIG. 6 is a flowchart illustrating operation of the mounting apparatus 100 illustrated in FIGS. 1 and 5, according to example embodiments.

The chip cassette 3, accommodating the IC chip 4, and the circuit board 8 may be prepared at desired (or, alternatively predetermined) positions, information for designating the IC chip 4 and the circuit board 8 may be set in the signal processor 1 through a desired (or, alternatively predetermined) input device (not shown), then an operator may instruct a desired (or, alternatively predetermined) operation, and thus the mounting apparatus 100 may start to operate. When the mounting apparatus 100 starts to operate, the signal processor 1 may set a desired (or, alternatively predetermined) value of the focal length of the zoom lens 33 with reference to the design information 14a of the IC chip 4 and the focal length control information 14c which are stored in the storage unit 14. Accordingly, the imaging magnification of the chip camera may be finely adjusted based on the design information of the set IC chip 4. (Step S100).

While a process of mounting the same IC chip 4 is continuously performed multiple times, the fine adjustment of the imaging magnification of the chip camera 2 in operation S100 may be performed once on the first IC chip 4. For example, the amount of fine adjustment of the imaging magnification may be set, for example, based on the following calculation results.

Referring to FIG. 4, the size PixSizeXa of the pixel Px in the X direction and the size PixSizeYa of the pixel Px in the Y direction after the fine adjustment may be calculated using the expressions below. The Expressions may include, from the pitch PitchX between the solder bumps 4a in the X direction and the pitch PitchY between the solder bumps 4a in the Y direction, and the size PixSizeX of the pixel Px in the X direction and the size PixSizeY of the pixel Px in the Y direction at a desired (or, alternatively predetermined) reference magnification. The reference magnification is a magnification at which the pitch of the solder bump 4a becomes an integer multiple of the pixel size. However, because the imaging magnification has the same value in the X direction and the Y direction, when the arrangement of the solder bumps 4a and the image sampling conform to each other only in one of the X direction and the Y direction, the amount of fine adjustment may be calculated only in that one direction.

$$PixSizeXa = PitchX/ax \text{ (but, } ax = PitchX/PixSizeX - kx)$$

$$PixSizeYa = PitchY/ay \text{ (but, } ay = PitchY/PixSizeY - ky)$$

A value of PitchX is set to a relative value based on the size of PixSizeX. A value of PitchY is set to a relative value based on the size of PixSizeY. $kx$ and $ky$ denote a constant for setting the amount of fine adjustment, and may be set based on, for example, the number N of arrangements of the solder bumps 4a. Thus, the relation of $kx=1/Nx$ (where Nx denotes the number of solder bumps 4a in the X direction) and the relation of ky=1/Ny (where Ny denotes the number of solder bumps 4a in the Y direction) may be satisfied.

Further, setting values of imaging magnification may be determined to be PixSizeXa/PixSizeX (magnification in the X direction) and PixSizeYa/PixSizeY (magnification in the Y direction). As described above, the size PixSizeXa denotes the size of the pixel Px in the X direction and PixSizeYa denotes the size of the pixel Px in the Y direction after the fine adjustment, and PixSizeX denotes the size of the pixel Px in the X direction and PixSizeY denotes the size of the pixel Px in the Y direction at a reference magnification. When the magnifications in the X direction and the magnification in the Y direction have different calculated values, the setting values of imaging magnification may be adjusted based on one of the calculated values. Alternatively, when a line sensor is used, if the calculated value in the X direction is set as imaging magnification and the PixSizeY in the Y direction may be finely adjusted by adjusting a moving speed at the time of imaging. Thus, any correspondence may be made even though the magnifications in the X direction and the magnification in the Y direction have different calculated values.

Figure 7:
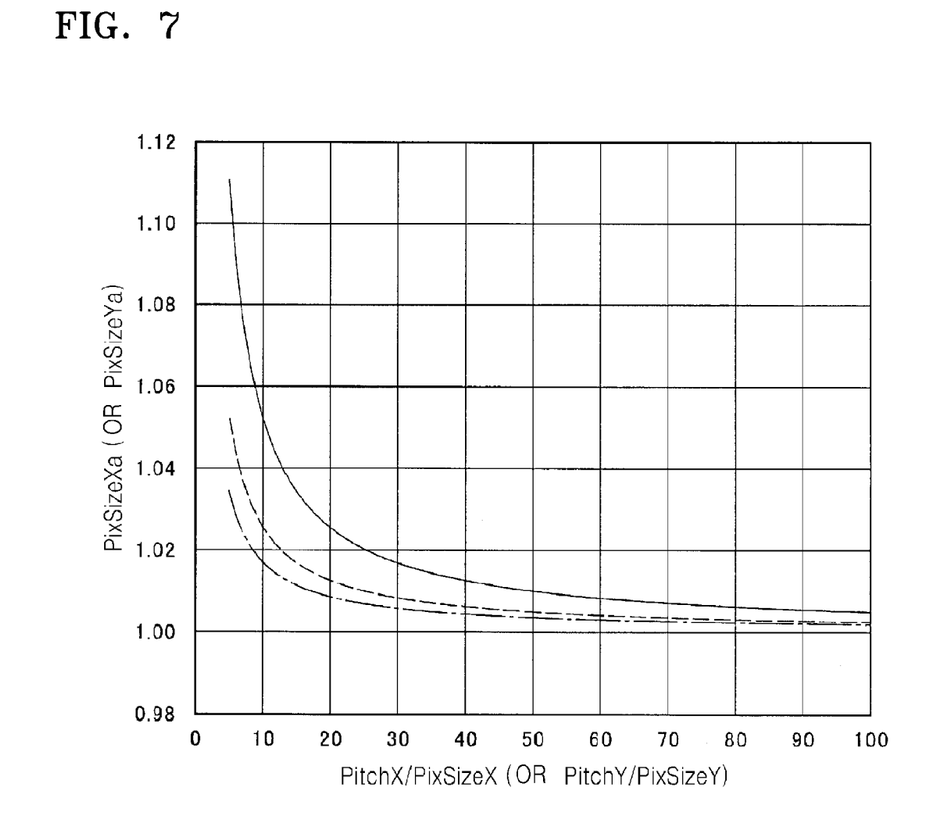
FIG. 7 is a diagram illustrating an example of the amount of fine-adjustment of a pixel size described with reference to FIG. 4.

FIG. 7 is a diagram illustrating an example of the amount of fine-adjustment of a pixel size described with reference to FIG. 4. Referring to FIG. 7, the calculation results of the amount of adjustment using the above-described expression is illustrated. A horizontal axis denotes a value of PitchX/PixSizeX (or PitchY/PixSizeY) and a vertical axis denotes a value of PixSizeXa (or PixSizeYa). A unit of the values is arbitrarily set such that the pixel size satisfies the relation of PixSizeX=PixSizeY=1. Referring to the calculated values shown in FIG. 7, a solid line indicates a case of N=2 (where N is the number of solder bumps 4a), a dotted line indicates a case of N=4, and a dot-dashed line indicates a case of N=6. Referring to FIG. 7, if an interval between the solder bumps 4a is 10 times the pixel size, the amount of fine adjustment may be 5% or less.

When the process of Step S100 is completed, the signal processor 1 may output a desired (or, alternatively predetermined) control signal to the motion controller 61 to move the movement unit 6 over the IC chip 4 to be adsorbed, on the chip cassette 3 (Step S101). Next, the motion controller 61 may pick up the IC chip 4 at the adsorption head 5 from the chip cassette 3 in response to an instruction from the signal processor 1 (Step S102). Then, the motion controller 61 may start to move the movement unit 6 toward the substrate stage 7 in response to an instruction from the signal processor 1 (Step S103). Here, the chip camera 2 may image the IC chip 4 in response to an instruction from the signal processor 1 (Step S104). Then, the signal processor 1 may calculate the amount of positional deviation of the IC chip 4 based on the image captured by the chip camera 2 (Step S105).

In Step S105, the signal processor 1 may calculate the amount of positional deviation and the amount of angular deviation of the IC chip 4, for example, in the following manner.

(1) First, the signal processor 1 may perform an image process for correcting grayscale luminance and lens aberration of a desired (or, alternatively predetermined) pixel of the image captured by the chip camera 2, with reference to information for correcting a variation in luminance and lens aberration, which are confirmed in advance. However, the correction process may be omitted depending on configurations.

(2) Next, the signal processor 1 may set regions to be recognized which correspond to the solder bumps 4a, based on a design value of the IC chip 4 stored in the storage unit 14.

(3) Then, the signal processor 1 may measure a position of the center of gravity of a luminance value from luminance values (=pixel values) of pixels for each of the recognized regions.

(4) Next, the signal processor 1 may measure the amount of deviation ($\Delta X$) of the IC chip 4 in the X direction, the amount of deviation ($\Delta Y$) in the Y direction, and the amount of angular deviation ($\Delta \theta$) thereof, based on X and Y coordinates of each solder bump 4a.

For example, the signal processor 1 may estimate an arrangement direction of the solder bumps 4a by using, for instance, a least-square method based on the X and Y coordinate values of the plurality of solder bumps 4a. Next, a coordinate of the center point Pc of the IC chip 4 may be measured based on the estimated arrangement direction of the solder bumps 4a. Further, the signal processor 1 may recognize the reference point 5b and the reference line 5c which are described above with reference to FIG. 3, and may measure a direction serving as a reference when measuring a coordinate of the reference point P0 and the amount of angular deviation $\theta$ based on the recognized reference point 5b and reference line 5c. Accordingly, the signal processor 1 may measure the amount of deviation $\Delta X$ in the X direction, the amount of deviation $\Delta Y$ in the Y direction, and the amount of angular deviation $\Delta \theta$.

Next, the signal processor 1 may output a desired (or, alternatively predetermined) instruction to the motion controller 61, and the motion controller 61 may move the movement unit 6 above a mounting position of the IC chip 4 in the circuit board 8 on the substrate stage 7 (Step S106). Next, the place camera 10 may image a mounting region of the IC chip 4 on the circuit board 8 in response to an instruction of the signal processor 1 (Step S107). The signal processor 1 may recognize the amount of positional deviation in the XY directions and the amount of angular deviation of the mounting position, with respect to a mounting region of the IC chip 4 in the image obtained by the place camera 10 (Step S108).

Then, the signal processor 1 may calculate the amount of correction of the movement unit 6, based on the amount of positional deviation and the amount of angular deviation of the IC chip 4, which are calculated in Step S105, and the amount of positional deviation of the mounting region of the circuit board 8 (Step S109). The signal processor 1 may calculate the amount of correction when adjusting positions and angles $\theta$ of the movement unit 6 in the X, Y, and Z directions taking in to account of the recognition results for the circuit board 8 such that the amounts of deviation of the IC chip 4 $\Delta X$, $\Delta Y$, $\Delta Z$, and $\Delta \theta$ conform to a reference position and a reference direction as much as possible.

Next, the signal processor 1 may transmit a signal for instructing each amount of correction calculated in Step S109 to the motion controller 61 (Step S110). After the motion controller 61 corrects the positional deviation or angular deviation of the movement unit 6, the movement unit 6 may descend, the IC chip 4 may be placed on the connection portion of the circuit board 8, and the IC chip 4 may be thermocompression-bonded to the circuit board 8 (Step S111).

As described above, according to example embodiments, the mounting apparatus 100 may include the zoom lens 33 as an imaging magnification adjustment unit, which is capable of changing imaging magnification. Further, the mounting apparatus 100 may include the chip camera 2 (imaging unit) as an imaging unit having a plurality of imaging pixels. The imaging unit may be configured to image the IC chip 4 (object to be recognized) having the plurality of solder bumps 4a (first objects to be recognized), which are arranged at desired (or, alternatively predetermined) intervals, through the zoom lens 33. Further, the mounting apparatus 100 may include the storage unit 14 that stores the design information 14a indicating shape information of the IC chip 4. The design information 14a may include at least information (PitchX of FIG. 4) indicating an arrangement interval between the plurality of solder bumps 4a. The mounting apparatus 100 may adjust imaging magnification of the zoom lens 33 based on the length of the imaging pixel (PixSizeX of FIG. 4) depending on the imaging pixel and the information indicating the arrangement interval between the solder bumps 4a stored in the storage unit 14. Further, the mounting apparatus 100 may include the signal processor 1 that recognizes the position of the solder bump 4a based on a plurality of pixel values in the image captured by the chip camera 2. Here, the signal processor 1 may adjust the imaging magnification so that the arrangement interval and an integer multiple of the length of the imaging pixel Px do not conform to each other in the image captured by the chip camera 2. Thus, according to example embodiments, the imaging magnification may be adjusted with respect to an object to be recognized. A shape in which the arrangement of objects to be recognized and the image sampling conform to each other is configured such that the arrangement of the objects to be recognized and the image sampling do not conform to each other. Accordingly, a decrease of the accuracy of position recognition, which may occur when a correspondence relationship between an arrangement of an object to be recognized and the image sampling satisfies a specific condition, may be reduced or prevented.

According to example embodiments, an adjustment mechanism of lens magnification may be configured as, for example, a motorized zoom, which is capable of perform an automatic adjustment. Thus, when the layout of the IC chip 4 is changed, the adjustment mechanism may automatically correspond to a layout of the IC chip 4 to be targeted. According to other example embodiments, a configuration may be made such that the focal length of the zoom lens 33 is set manually.

According to example embodiments, an image may be acquired as rotating the chip camera 2. In this method, a rotation axis may rotate before and after the mounting of the IC chip 4, and thus a mounting time of the IC chip 4 may be affected. Thus, when lens magnification is finely adjusted, the fine adjustment may be performed only once before a process is performed so that a mounting time of the IC chip 4 may not be affected.

In addition, an expansion may be made so that magnification adjustment is independently performed in a two-dimensional direction, by including a lens (for example, a cylindrical lens), which has a focal length varying depending on an axial direction in a plurality of lens groups constituting the zoom lens 33.

Although bumps arranged at equal intervals have been described, but the intervals are not limited thereto. A pixel size in which a variation is maximized when fine adjustment of the pixel size is performed by using a variation having a value equal to or less than a decimal point as a target function may be selected as a magnification adjustment value when an adjusted pixel size is numerically a real number rather than an integer number.

Although the solder bump 4a on the IC chip 4 may be used as an object to be recognized, but an object to be recognized is not limited thereto. Position recognition using the chip camera 2 may be applied to, for example, a semiconductor chip using packaging other than a CSP, another component mounted on a circuit, or a passive component. Further, example embodiments are not limited to the mounting apparatus, but may also be configured as, for example, an apparatus used in a process of inspecting the solder bump 4a in an operation before the solder bump 4a is accommodated in the chip cassette 3. Furthermore, the chip camera 2 may be configured to use an area sensor instead of the line sensor 21.

According to example embodiments, imaging magnification may be adjusted with respect to an object to be recognized. A shape in which the arrangement of objects to be recognized and the image sampling conform to each other is configured such that the arrangement of the objects to be recognized and the image sampling do not conform to each other. Accordingly, a decrease in the accuracy of position recognition, which may occur when a correspondence relationship between an arrangement of an object to be recognized and the image sampling satisfies a specific condition, may be reduced or prevented.

While example embodiments have been particularly shown and described with reference to the example embodiments thereof, it will be understood by one of ordinary skill in the art that various changes in form and details may be made therein without departing from the spirit and scope of example embodiments defined by the following claims.

What is claimed is:

1. A recognition and mounting apparatus comprising:
    an imaging magnification adjustment unit configured to change an imaging magnification;
    an imaging unit having a plurality of imaging pixels and configured to capture an image an object to be recognized through the imaging magnification adjustment unit, the object having a plurality of recognizable features to be recognized, the recognizable features provided at at least one arrangement interval;
    a storage unit configured to store a shape information of the object, the shape information including at least information indicating the arrangement interval between the recognizable features; and
    a signal processor configured to adjust the imaging magnification of the imaging magnification adjustment unit based on a length of the imaging pixels and the shape information stored in the storage unit, and configured to recognize positions of the recognizable features based on a plurality of pixel values in the image captured by the imaging unit.

2. The recognition and mounting apparatus of claim 1, wherein the signal processor is configured to adjust the imaging magnification of the imaging magnification adjustment unit such that the arrangement interval and an integer multiple of the length of the imaging pixel do not conform to each other in the image captured by the imaging unit.

3. The recognition and mounting apparatus of claim 2, further including:
    a mounting apparatus configured to mount the object to be recognized to a circuit board by performing a correction control according to a position or an angle of the object to be recognized, based on results of the recognizing by the signal processor.

4. The recognition and mounting apparatus of claim 1, wherein the signal processor includes:
    an input unit;
    an output unit;
    a storage unit; and
    a host computer having a central processing unit.

5. The recognition and mounting apparatus of claim 4, wherein the signal processor further includes a main memory having an image memory therein.

6. The recognition and mounting apparatus of claim 4, wherein the signal processor is configured to execute program stored in the storage unit.

7. The recognition and mounting apparatus of claim 4, wherein the input unit is configured to input a signal from the imaging unit to the host computer, and the output unit is configured to output a signal from the host computer to change the imaging magnification of the imaging magnification adjustment unit.

8. The recognition and mounting apparatus of claim 1, further comprising:
   a mounting apparatus configured to mount the object to be recognized to a circuit board by performing correction control according to a position or an angle of the object to be recognized, based on results of the recognizing by the signal processor.

9. The recognition and mounting apparatus of claim 1, wherein the object includes a semiconductor chip.

10. A recognition and mounting method comprising:
    changing an imaging magnification using an imaging magnification adjustment unit;
    capturing an image, using an imaging unit having a plurality of imaging pixels, an object having a plurality of recognizable features through the imaging magnification adjustment unit, the recognizable features provided at at least one arrangement interval;
    storing, using a storage unit, a shape information of the object, the shape information including at least one of the arrangement interval;
    adjusting, using a signal processor, the imaging magnification of the imaging magnification adjustment unit based on a length of the imaging pixel and the shape information stored in the storage unit; and
    recognizing, using the signal processor, positions of the recognizable features based on a plurality of pixel values in the image captured by the imaging unit.

11. The recognition and mounting method according to claim 10, the method further comprising:
    adjusting, using the signal processor, the imaging magnification of the imaging magnification adjustment unit such that the arrangement interval and an integer multiple of the length of the imaging pixel do not conform to each other in the image captured by the imaging unit.

12. The recognition and mounting method of claim 11, the method further comprising:
    mounting the object to be recognized onto a circuit board by performing a correction control according to a position or an angle of the object to be recognized, based on results of the recognizing.

13. The recognition and mounting method of claim 10, the method further comprising:
    mounting the object to be recognized onto a circuit board by performing correction control according to a position or an angle of the object to be recognized, based on results of the recognizing.

* * * * *